United States Patent [19]
So et al.

[11] Patent Number: 5,817,314
[45] Date of Patent: Oct. 6, 1998

[54] QUILLAJA SAPONIN ADJUVANT AND VACCINE FORMULATION CONTAINING SAME

[75] Inventors: Hong-Seob So, Daejeon; Hye-Sung Yoon, Kyunggi-do; Young-Sun Kwon; Joong-Myung Cho, both of Daejeon, all of Rep. of Korea

[73] Assignee: LG Chemical Ltd., Seoul, Rep. of Korea

[21] Appl. No.: 750,461

[22] PCT Filed: Apr. 12, 1996

[86] PCT No.: PCT/KR96/00053

§ 371 Date: Dec. 6, 1996

§ 102(e) Date: Dec. 6, 1996

[87] PCT Pub. No.: WO96/32401

PCT Pub. Date: Oct. 17, 1996

[30] Foreign Application Priority Data

Apr. 13, 1995 [KR] Rep. of Korea ............... 1995/5890
Apr. 13, 1995 [KR] Rep. of Korea ............... 1995/8589

[51] Int. Cl.$^6$ ........................ A61K 39/00; A61K 39/29; C07G 3/00; C07H 15/24
[52] U.S. Cl. ...................... 424/184.1; 424/225.1; 514/25.1; 514/26.1; 514/33.1; 514/35.1; 536/4.1; 536/6.3

[58] Field of Search ............... 424/225.1, 184.1; 514/25, 26, 33, 35; 435/5; 536/4.1, 6.3

[56] References Cited

U.S. PATENT DOCUMENTS 5,057,540  10/1991  Kensil et al. .......................... 514/25

OTHER PUBLICATIONS

Kensil et al. 1991 J Immunol. 146 (2) 431–437, Jan. 15, 1991.
Newman et al. 1992 AIDS Res. Hum Retrovir. 8 (8) 1413–1418, Aug. 1, 1992.
Ronnberg et al. 1995 Vaccine 13 (14) 1375–1382, Jul. 1, 1995.

*Primary Examiner*—Michael P. Woodward
*Assistant Examiner*—Mary K. Zeman
*Attorney, Agent, or Firm*—Anderson, Kill & Olick, P.C.

[57] ABSTRACT

A novel saponin component having a molecular weight of about 956 daltons, a process for isolating the saponin component from the bark of *Quillaja saponaria Molina*, a vaccine formulation comprising the saponin component as an immune adjuvant, a method for increasing the immune response to an antigen by employing an adjuvant composition comprising saponin component and a second adjuvant.

10 Claims, 7 Drawing Sheets

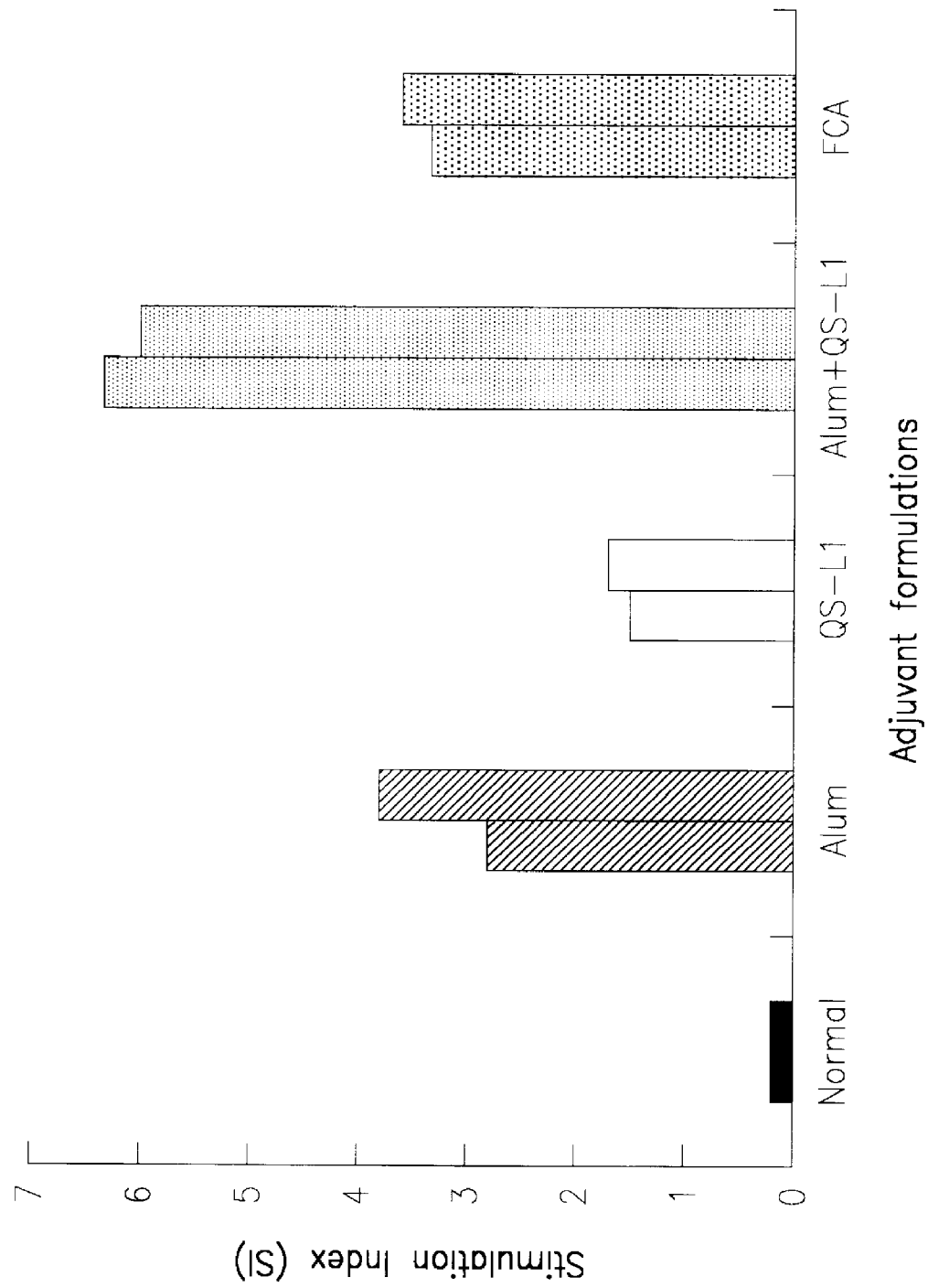

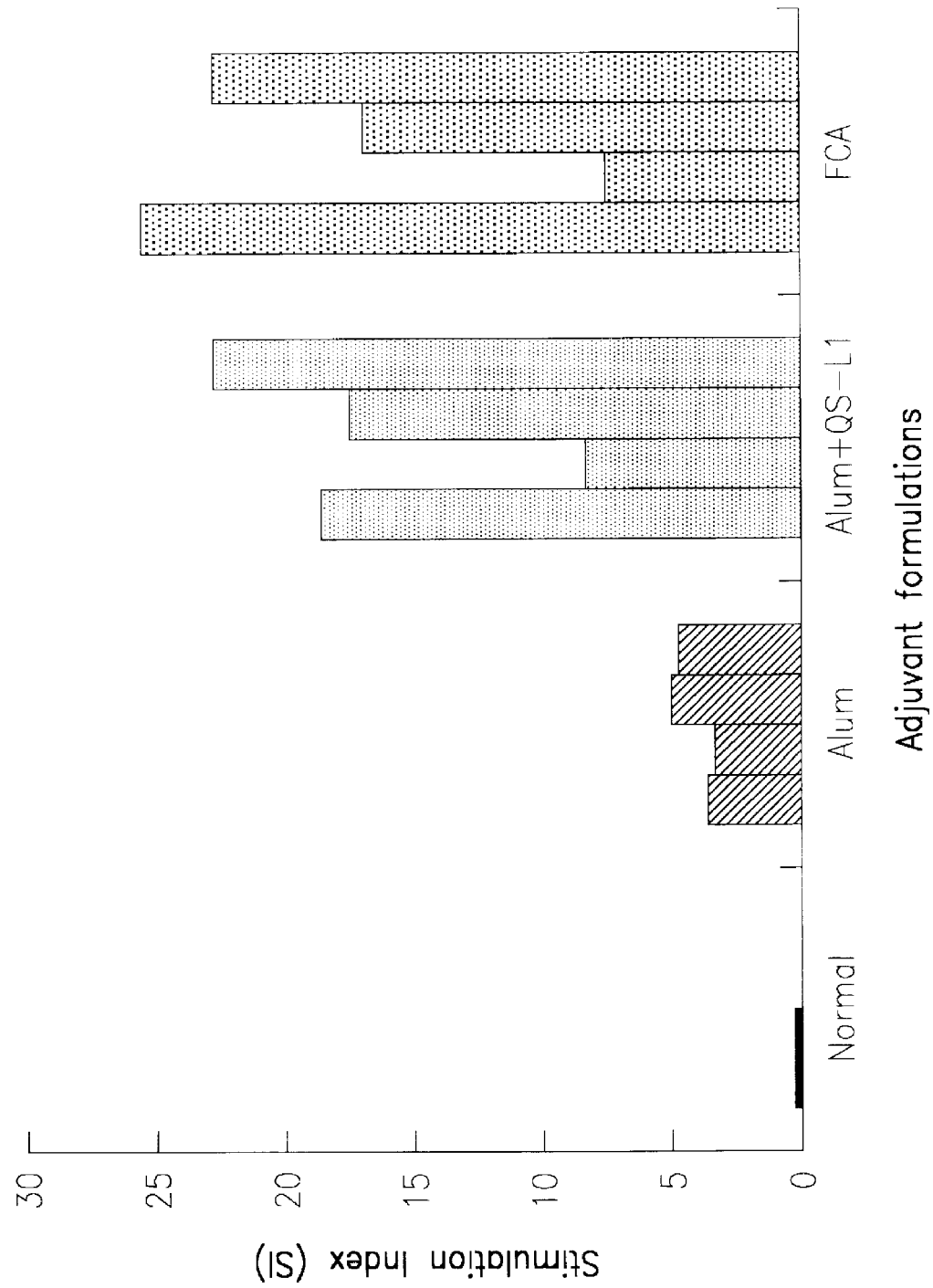

QUILLAJA SAPONIN ADJUVANT AND VACCINE FORMULATION CONTAINING SAME

FIELD OF THE INVENTION

The present invention relates to a novel saponin component and a vaccine formulation comprising same as an immune adjuvant. More specifically, it pertains to a novel saponin component having a molecular weight of about 956 daltons, a process for isolating the saponin component from the bark of *Quillaja saponaria Molina*, a vaccine formulation comprising the saponin component as an immune adjuvant, a method for increasing the immune response to an antigen by employing an adjuvant composition comprising the saponin component and a second adjuvant.

BACKGROUND OF THE INVENTION

Bioengineering technologies have made significant contributions to the development of vaccines which contain recombinant antigens derived from various viral coat proteins. However, vaccines effective in preventing such threatening diseases as those caused by HIV(Human Immunodeficiency Virus) and HCV(Hepatitis C Virus) have not yet become available due partly to the lack of adjuvants effective in boosting the relatively weak antigenicity of the recombinant antigens. Therefore, extensive studies have been carried out to develop adjuvants suitable for use in such vaccines.

Currently, aluminum hydroxide(alum) is the only available adjuvant approved for human use because of its low toxicity. However, alum has been known to be ineffective when used with antigens for diseases caused by HIV, HCV, HSV(Herpes Simplex Virus) as well as schistosomiasis, whooping cough and typhoid(Sanchez-Pescador et al., *J. Immunol.*, 141, 1720–1727(1988); James, S. L., et al., ibid., 140, 2753–2759(1988); Edelman R., *Rev. Infect. Dis.*, 2, 370–383(1980)). A need to develop new adjuvants has thus been recognized, and in response to this need, there have been proposed a number of adjuvants, e.g., saponins, oil emulsions, monophosphoryl lipid A and Freund's adjuvants. However, each of these adjuvants has been found to have the problem of unsatisfactory adjuvant activity, high toxicity and/or undesirable adverse effects. Freund's adjuvant, for example, may cause granulomatous inflammation, while saponins described in the prior art tend to suffer from the toxicity problem as described below.

Saponins are plant glycosides which have many commercial uses such as foaming agents in beverages, detergents in the textile industries and others. It has been recently shown that a mixture of Quillaja saponins obtained by extracting the bark of the South American tree, *Quillaja saponaria Molina*, exhibits humoral and cellular immune responses (Espinet R. G., *Gac. Vet.*, 13, 268–273 (1951); Dalsgaard K., *Arch. Gesamte Virus Forsch.*, 44, 243–254(1974); Morein B., *Nature*, 322, 287–288(1988)). A purified form of Quillaja saponins is commercially available under the name, "Quil-A"(Iscotec AB, Sweden; and Superfos Biosector a/s, Frydenlundsvej 30, DK-Vedbaek, Denmark).

Quil-A is, however, a mixture of a large number of homologous glycosides which may be represented by the general chemical structure wherein triterpenoid quillaic acid, the aglycone, is bonded to a sugar moiety of various type and length through a glycosidic linkage. It is also known that each of these glycosidic components displays widely varying adjuvant activity and toxicity, and therefore, Quil-A is not safe for use in pharmaceutical formulations for man(Kersten et al., *Infect. Immun.*, 56, 432–438(1988)). Accordingly, there have been attempts to identify only the safe and effective Quillaja saponin components and to develop a method for preparing thereof.

Kensil et al. subjected the methanol soluble fraction of a crude Quillaja bark extract to reversed phase high pressure liquid chromatography("RP-HPLC") using a 40 mM acetic acid solution in methanol/water(58:42(v/v)) and obtained several purified saponin components. Among those, a component designated QS-18 was found to show a high hemolytic activity, i.e., highly toxic. Another component having the QS-21 designation, on the other hand, had a low toxicity while showing a high adjuvant activity. Also reported to posses adjuvant effects are components designated QS-7 and QS-17(Kensil et al., *J. Immunol.*, 146, 431–437(1991); Kensil et al., U.S. Pat. No. 5,057,540 (1991)). It has been further reported that the component QS-21 enhances the immunogenicity of the HIV and other viral antigens(Kensil et al., *JAMA*, 199, 1423–1427(1991); Wu, J. W., et al., *J. Immunol.*, 148, 1519–1525(1992)).

However, the preparation method disclosed by Kensil et al. is unduly complicated requiring the combined use of silica gel chromatography and RP-HPLC. Moreover, the isolated QS-7, QS-17, QS-18 and QS-21 components have molecular weights ranging from 1,800 to 2,600 daltons, representing only a portion of the Quillaja saponins present in the bark extract.

Kersten et al., on the other hand, have employed hydrophobic RP-HPLC to isolate more than 23 components of Quil-A. One particular component having the designation of QA-3 was found to be superior to QS-21 in terms of both toxicity and adjuvant activity when used together with a sterol, a phospholipid and an antigen in the form of a two- or three-dimensional immunogenic complex(Kersten et al., WO 92/06710).

However, the sterol contained in the immunogenic complexes of Kersten et al. is not approved for use in an injection formulation. Further, all components isolated and disclosed by Kersten et al., including QA-3, represent only the saponins having molecular weights ranging from 1,300 to 2,400 daltons. Thus, the prior studies have been silent about the possibility of finding an effective and safe adjuvant in other portions of the Quillaja bark extract, particularly a lower molecular weight Quillaja saponin component.

SUMMARY OF THE INVENTION

Accordingly, it is an object of the present invention to provide a novel saponin component which has no or little toxicity and exhibits a high adjuvant activity when used in a vaccine.

Another object of the present invention is to provide a process for isolating said saponin component from the bark of *Quillaja saponaria Molina*.

An additional object of the present invention is to provide a vaccine formulation comprising the saponin component as an adjuvant optionally with another adjuvant.

A further object of the present invention is to provide a method for increasing the immune response to an antigen in a vaccine formulation by employing the saponin component as an adjuvant optionally with a second adjuvant.

In accordance with one aspect of the present invention, there is provided a saponin component, designated QS-L1, having a molecular weight of about 956 daltons, which is isolated from the bark of *Quillaja saponaria Molina* and has no or little toxicity while exhibiting a high synergistic adjuvant activity when combined with a second adjuvant.

BRIEF DESCRIPTION OF THE DRAWINGS

The above and other objects and features of the present invention will become apparent from the following description of the invention, when taken in conjunction with the accompanying drawings, in which:

FIGS. 6A and 6B compare the observed adjuvant activities of QS-L1 as QS-L1/alum with those of alum and Freund's complete adjuvant(FCA) in immunization with the antigen HBsAg.

DETAILED DESCRIPTION OF THE INVENTION

Figure 1:
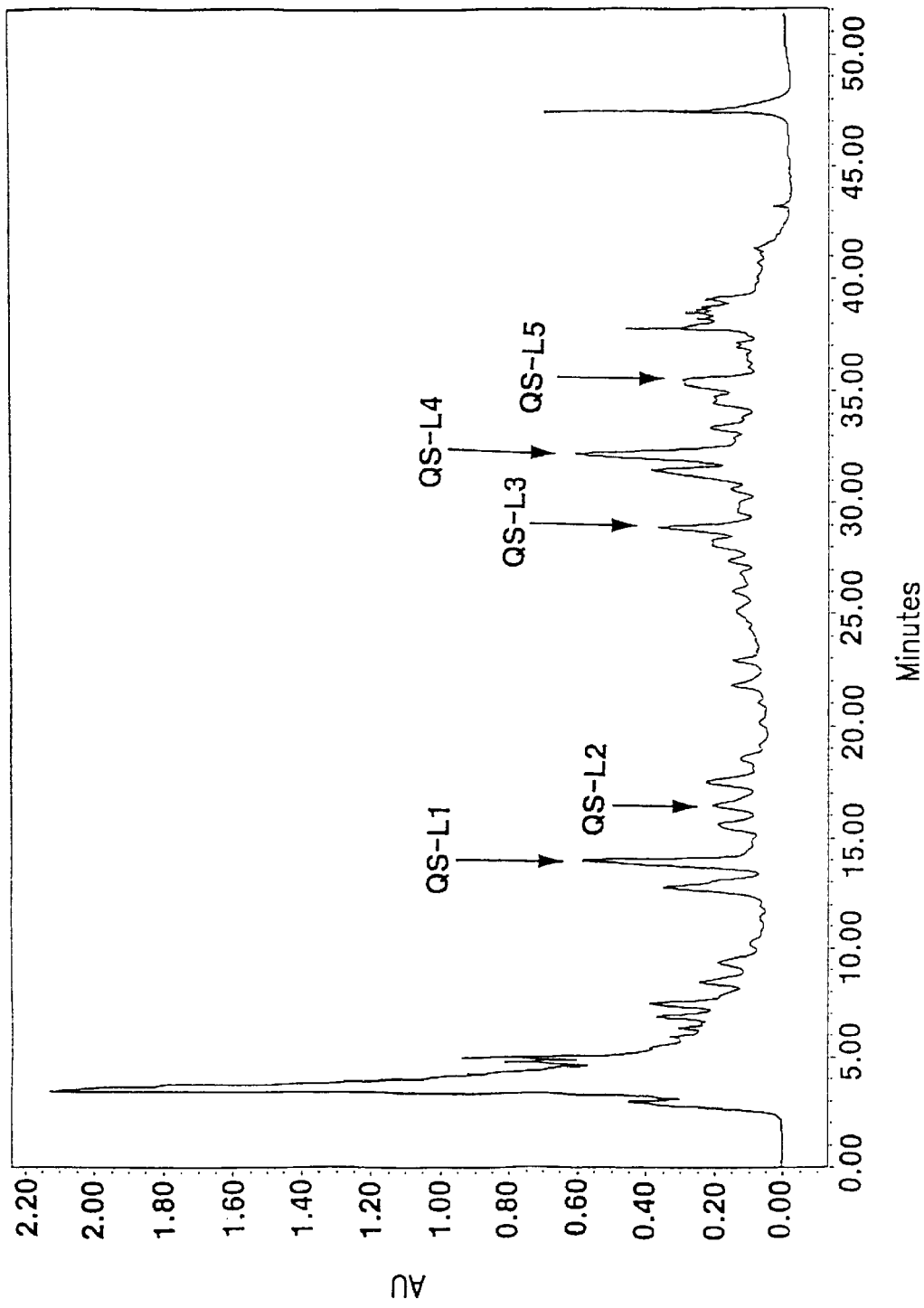
FIG. 1 shows the RP-HPLC scan of a bark extract of *Quillaja saponaria Molina*.
Figure 2:
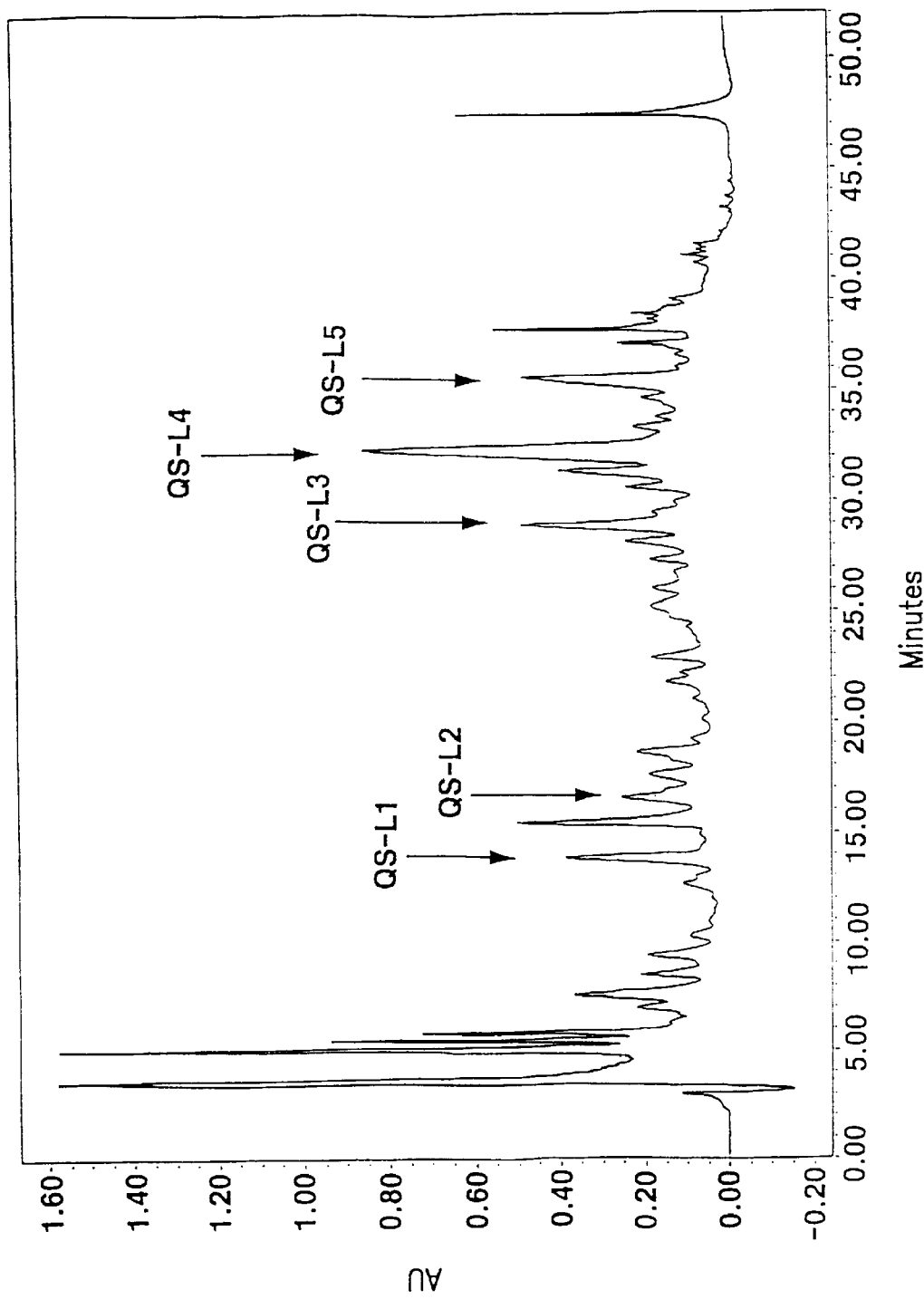
FIG. 2 depicts the RP-HPLC scan of Quil-A.

The saponin component of the present invention, i.e., QS-L1, may be isolated from the bark of *Quillaja saponaria Molina* and has no or little toxicity while exhibiting a surprisingly high immune adjuvant activity when combined with another adjuvant, e.g., alum.

The term "immune adjuvant" as used herein refers to a compound which, when administered together with an antigen to man or tested in vitro, enhances the subject's immune response to the antigen.

QS-L1 may be characterized by a molecular ion at m/z 979.4 when analyzed by mass spectrometry using the electron spray ionization method(ESI-MS) as well as by a retention time of about 13.98 min. when analyzed by reversed phase high pressure liquid chromatography on a 4.6×250 mm Vydac C4 column using a 0.1 wt % aqueous trifluoroacetic acid solution in water/acetonitrile(7:3(v/v)) at a flow rate of 1 ml/min.

The present invention also provides a process for isolating QS-L1 from the bark of *Q. saponaria Molina*, which may be summarized as follows. First, a bark extract of *Q. saponaria Molina* is prepared by treating the cambium layer of *Q. saponaria Molina* with water and lyophilizing the crude extract.

Then, QS-L1 may be purified from the bark extract of *Q. saponaria Molina* by a process which comprises:

(a) centrifuging a solution of the bark extract in an aqueous acetic acid solution to obtain a supernatant;

(b) dialyzing the supernatant against the aqueous acetic acid solution using an ultradialysis membrane;

(c) centrifuging the resulting dialyzate to obtain a supernatant;

(d) lyophilizing the supernatant to obtain a saponin extract powder; and (e) dissolving the saponin extract powder in a suitable solvent and subjecting the solution to RP-HPLC to obtain a fraction containing substantially pure QS-L1.

Concentration of the aqueous acetic acid solution in Step (a) may ranges from 10 to 100 mM, preferably, 40 mM. The molecular cut-off value of the dialysis membrane used in Step (b) may range from 12 to 14 kDa, which is suitable for the removal of low-molecular weight, water-soluble contaminants. The fractionation with RP-HPLC in step (e) is preferably carried out by using a C4 RP-HPLC column as well as an aqueous 0.1% trifluoroacetic acid solution as the eluent, under a linear concentration gradient of 30 to 40% acetonitrile containing 0.1% trifluoroacetic acid.

The RP-HPLC scan of the bark extract shows more than 32 peaks. A number of those peaks can be cleanly separated through preparative fractionation to provide various saponin components of high purity, including a novel, low molecular weight saponin component which is named QS-L1. QS-L1 elutes at a retention time of 13.98 min. when a 4.6×250 mm Vydac C4 column is used. An ESI-MS analysis of QS-L1 shows a molecular ion at m/z 979.4 and after subtracting the contributing by Na, the molecular weight of QS-L1 is deduced to be about 956 daltons.

QS-L1 may also be separated from other Quillaja extracts, e.g., Quil-A(Superfos Biosector a/s, Frydenlundsvej 30, DK-Vedbaek, Denmark), by using the same RP-HPLC method described as above.

The toxicity of QS-L1 may be determined from the intraperitoneal injection dose that brings death to mice within 72 hours. Such experiments show that QS-L1 is not lethal to mice at a dose level of up to 500 $\mu$g.

QS-L1, when used alone with an antigen, shows a low immune adjuvant activity relative to some of the saponin components known in the art, e.g., QS-21. However, QS-L1 shows a remarkably high immune adjuvant activity when used in combination with another marginal adjuvant, e.g., alum. This sort of strong synergistic interaction between two or more kinds of adjuvants has never been observed up to this point.

Accordingly, the present invention also provides a vaccine formulation comprising an antigen and an adjuvant composition comprising QS-L1 and another adjuvant, preferably, alum. Alum is preferably in the form wherein the antigen is adsorbed thereto. Antigens suitable for use in the present invention are not limited to any particular class of antigens and these include hepatitis B viral surface antigen, HIV and HCV antigens, and others. The concentration of an antigen in the formulation of the present invention may be adjusted in accordance with various factors, for instance, antigen species, required level of antigenicity, specifics of the subject to be inoculated and desired degree of immunization.

The vaccine formulation of the present invention may be in the form of an injectable solution or suspension, which may be prepared in accordance with any of the conventional procedures. The formulation may further comprise pharmaceutically acceptable excipients, carriers or diluents. Suitable excipients may comprise water, saline, dextrose, glycerol, ethanol, and a mixture thereof. Further, the composition may additionally comprise wetting agents, emulsifying agents, pH buffers, and the like.

A typical single dose of the vaccine formulation may vary in accordance with the form of the formulation, and should be determined in light of various relevant factors mentioned above. The amount of QS-L1 in the vaccine formulation of the present invention may range from 1 to 500 $\mu$g/single dose, preferably 10 to 50 $\mu$g/single dose, and that of alum, preferably 50 to 500 $\mu$g/single dose.

Further, the present invention provides a method for increasing the antigenicity of an antigen in said vaccine formulation by employing the saponin component QS-L1 as an immune adjuvant in combination with a second adjuvant, preferably, alum.

The following Reference Example and Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

REFERENCE EXAMPLE

Determination of Immune Adjuvant Activity of Saponin Component

A hepatitis B viral surface antigen(HBsAg) adsorbed on alum was prepared in accordance with the method for preparing commercialized EuVax(LG Chemical Ltd., Korean Patent No. 38837). HBsAg and alum(3% aluminum hydroxide) were mixed in a ratio of 100 μg of HBsAg to 2500 μg of alum, in 10 mM sodium phosphate buffer(1.2 mM $Na_2HPO_4.7H_2O$, 8.8 mM $K_3PO_4$, 0.8% NaCl, pH 6.3–6.5) and the mixture was stirred for 6 hours in an orbital shaker("Red Rotor", Hoefer, U.S.A.) to obtain HBsAg adsorbed on alum.

Then, the immune adjuvant activity of a saponin component was determined by using the HBsAg adsorbed on alum as follows. A saponin component was dissolved in distilled water to a concentration of 2 mg/ml. A HBsAg vaccine injection was prepared by adding 50 μl of the saponin solution to 1 ml of HBsAg adsorbed on alum(100 μg HBsAg/2500 μg alum). 50 μl each of vaccine injections were injected subcutaneously to two spots in the back of a 7 to 8-week old female Balb/c mouse(Charle's River Institute, Japan) and, the mouse was subjected to two serial boost shots each employing the same amount of vaccine injection, at 3-week intervals. A blood sample was taken from the tail of the mouse 17 days after the last boosting and the titer of antibody formed against the HBsAg was determined as follows.

Purified HBsAg was dissolved in 50 mM sodium borate buffer(pH 9.0) to a concentration of 0.5 μg/ml. The solution was added to the wells of a microtiter plate (Immulon type 1 microtiter plate, Dynatech, U.S.A.) in an amount of 200 μl/well and incubated at 37° C. for 2 hours. Phosphate buffered saline(PBS) containing 0.2% (w/v) gelatin was then added to the wells in an amount of 250 μl/well. The plate was incubated at 37° C. for 1 hours to block the remaining protein adsorption sites so as to prevent any non-specific reactions which may occur later. The wells were washed twice with PBS containing 0.05% (v/v) Tween-20 ("washing solution"). The blood sample taken from the mouse was diluted 400-fold with PBS containing 0.25% (w/v) gelatin, 1.0 mM EDTA, 1% (v/v) Triton X-100 and 0.02% (v/v) thimerosal("diluting solution"), further diluted by serial double dilution with the diluting solution up to final 819, 200-fold and added to the wells.

The wells of the plate incubated at 37° C. for 2 hours were washed five times with the washing solution; and a solution comprising anti-mouse IgG antibody labelled with horseradish peroxidase(HRP)(American Qualex, Cat. No. A106PS, U.S.A.), which was diluted 4,000-fold with said diluting solution, was added to the wells in an amount of 200 μl/well.

The resultant was incubated at 37° C. for 2 hours and washed 5 times with said washing solution. Thereafter, 200 μl of substrate solution, which was prepared by dissolving o-phenylene diamine dihydrochloric acid(OPD) tablet (Sigma, U.S.A.) with 50 mM citrate/phosphate buffer(pH 5.5) to a concentration of 2 mg/ml, was added to each well and the plate was incubated at room temperature for 30 min. in the dark. To the resultant was added 50 μl of 4N sulfuric acid per well to stop the color development; and O.D. of each well was determined at 492 nm with Titertech Multiscan Plus (Flowlab).

The antibody titer was determined as a reciprocal of the dilution multiple required for the O.D. value to reach 0.5.

EXAMPLE 1

Isolation of Saponin Components from *Quillaja saponaria Molina*

(Step 1) Preparation of Purified Saponin Extract

The bark of *Q. saponaria Molina* was extracted with water and the extract containing more than 50% saponin thus obtained was purchased from the Berghansen Corp. (Cincinnati, Ohio, U.S.A.). This saponin powder was dissolved in 40 mM aqueous acetic acid solution to a concentration of 250 mg/ml. The resulting solution was centrifuged by using a centrifuge(Beckman J2-21, JA 14) at 12,000 rpm for 30 min. to remove insoluble materials. The supernatant was dialyzed twice against 50-fold volume of 40 mM acetic acid solution by using an ultradialysis membrane (Spectrum Medical Industries Inc., Cat. No. 132676) having a molecular cut-off value ranging from 12 to 14 kDa to remove low-molecular weight, water-soluble materials. The dialyzate was centrifuged again to completely remove insoluble contaminants and the supernatant was lyophilized to obtain a purified saponin powder.

Silica gel thin layer chromatography of the saponin extract thus obtained suggested that the composition and purity of the extract are very similar to those of Quil-A.

(Step 2) Isolation of Saponin Components by C4 RP-HPLC

The saponin extract obtained in (Step 1) was dissolved in 0.1% aqueous trifluoroacetic acid(TFA) solution to a concentration of 20 mg/ml. 0.1 ml of the resulting solution was passed through a C4 RP-HPLC column(Vydac, 4.6×250 mm) which was pre-equilibrated with 0.1% aqueous TFA solution at a flow rate of 1 ml/min. The bound saponin was eluted by employing the acetonitrile concentration gradient shown in Table I and the eluates were detected at 214 nm.

TABLE I

| No. | Time | Flow rate (ml) | % A* | % B** |
| --- | --- | --- | --- | --- |
| 1 | 0.00 | 1.00 | 70.0 | 30.0 |
| 2 | 5.00 | 1.00 | 70.0 | 30.0 |
| 3 | 30.00 | 1.00 | 60.0 | 40.0 |
| 4 | 35.00 | 1.00 | 0.0 | 100.0 |
| 5 | 40.00 | 1.00 | 0.0 | 100.0 |
| 6 | 41.00 | 1.00 | 70.0 | 30.0 |
| 7 | 51.00 | 1.00 | 70.0 | 30.0 |
| 8 | 52.00 | 0.00 | 70.0 | 30.0 |

A*0.1% TFA in distilled water.
B**0.1% TFA in acetonitrile.

More than 32 saponin components were observed to elute at different retention times. Fractions were collected according to the retention times to obtain a number of pure saponin components. The relative ratio of each saponin component in the saponin extract variously ranged from 0.13 to 32%.

The immune adjuvant activities of the purified saponin components were determined in accordance with the method of Reference Example, and five components showing relatively high immunogenicity enhancing activities were designated QS-L1, QS-L2, QS-L3, QS-L4 and QS-L5, respectively. The area(%) of the peaks corresponding to the five components and retention times thereof are shown in Table II. The positions of the peaks corresponding to the five components are shown in FIG. 1.

TABLE II

| Component | Retention time (min.) | Area (%) |
|---|---|---|
| QS-L1 | 13.967 | 4.23 |
| QS-L2 | 16.483 | 1.45 |
| QS-L3 | 28.900 | 2.01 |
| QS-L4 | 32.233 | 5.27 |
| QS-L5 | 35.500 | 2.40 |

Each fraction containing QS-L1, QS-L2, QS-L3, QS-L4 or QS-L5 was lyophilized and the same RP-HPLC procedure as above was repeated to obtain the corresponding component in a purity ranging from 90 to 97%.

When the same RP-HPLC procedure was applied to Quil-A (Superfos Biosector a/s, Frydenlundsvej 30, DK-Vedbaek, Denmark), the same set of saponin components as above was observed, except that the relative ratios of the components were different from those obtained for the bark extract.

(Step 3) Silica Gel Thin Layer Chromatography of Purified Saponin Component

1 μg each of saponin components QS-L1, QS-L2, QS-L3, QS-L4 and QS-L5 obtained in (Step 2) and 40 μg of Quil-A(Superfos Biosector a/s, Frydenlundsvej 30, DK-Vedbaek, Denmark) were placed on silica gel thin layer chromatography plate(Si60 HPTLC, E. M. Science) and eluted for 3 to 4 hours by using a mixture of chloroform/methanol/distilled water (62:32:6(v/v/v)) as a developing solution.

Figure 3:
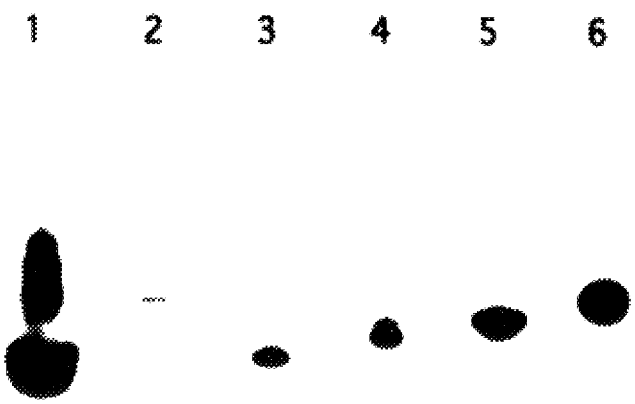
FIG. 3 displays the results of silica gel thin layer chromatography(TLC) analyses of Quil-A and purified saponin components QS-L1, QS-L2, QS-L3, QS-L4 and QS-L5.

The plate was dried at 80° C. for about 1 hour and, thereafter, Bial's reagent(Orcinol Ferric Chloride, Sigma, Cat. No. 0-7875) was sprayed on it to elicit a color development. The plate was then dried at 80° C. for 30 min. to selectively stain the sugar moieties of the saponin components. The result is shown in FIG. 3, wherein line 1 is Quil-A and lines 2 to 6 are QS-L1, QS-L2, QS-L3, QS-L4 and QS-L5, respectively. Each saponin component is shown as a single band.

EXAMPLE 2

Mass Spectrometry

Figure 4:
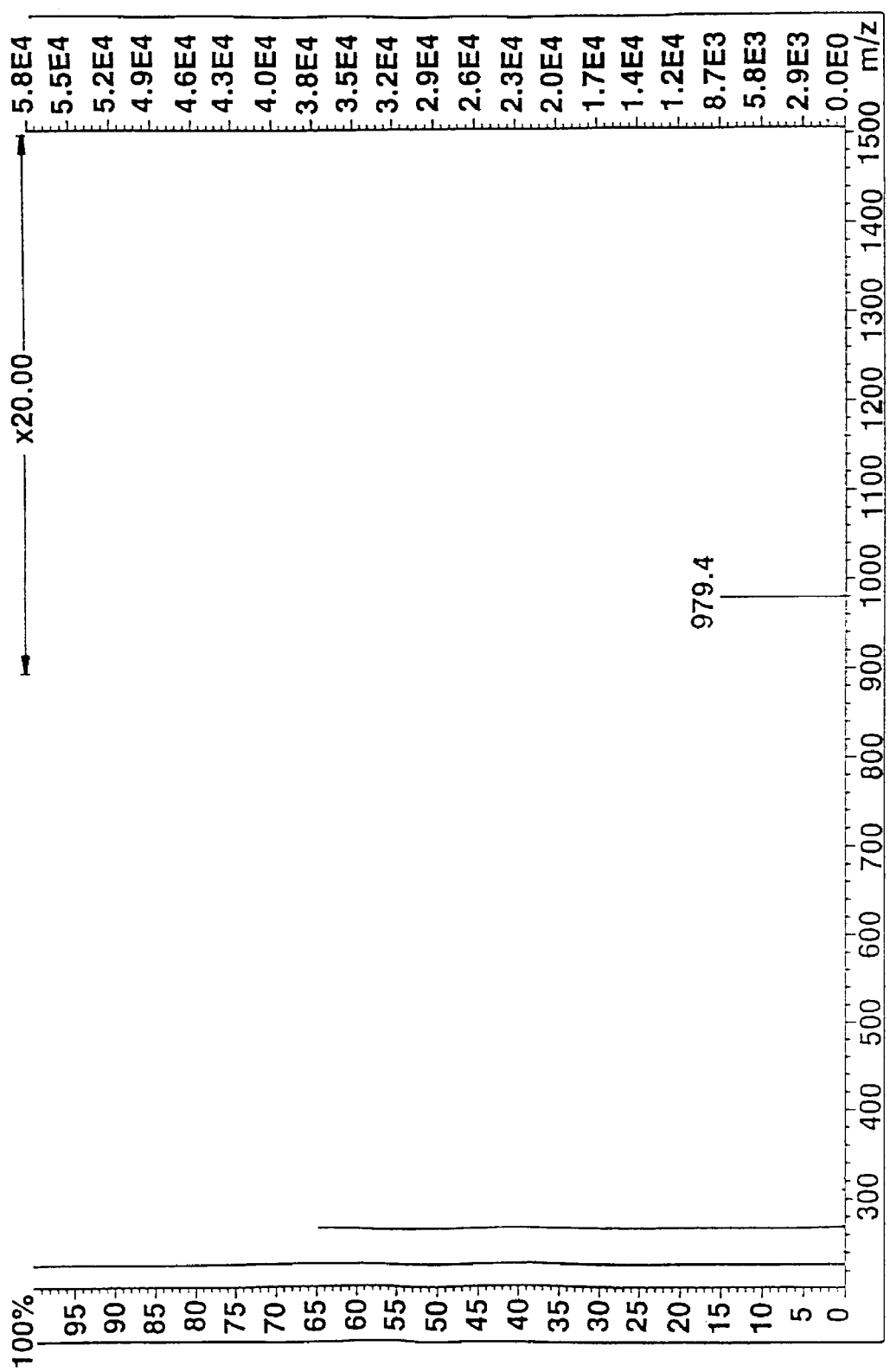
FIG. 4 reproduces the result of electron spray ionization-mass spectroscopy(ESI-MS) analysis of QS-L1.

The molecular weight of saponin component QS-L1 was determined with a VG Quattro LC/MS(Vacuum Generator, UK) using Electron Spray Ionization(ESI)-MS method, by employing acetonitrile/distilled water/acetic acid(60:40:0.5 (v/v/v)) as an eluent. As a result, an [M+Na]$^+$ ionic molecular peak was detected at 979.4 (m/z) as shown in FIG. 4. However, a sodium ion is enclosed therein and, accordingly, the (m/z) value should be reduced by 23. Therefore, the molecular weight of pure QS-L1 was determined to be about 956 daltons, which is much smaller than the molecular weight of QA-3, i.e., 1862 daltons, disclosed by Kersten et al.(WO 92/06710). Further, it considerably differs from the molecular weights of QS-17, QS-18 and QS-21, i.e., 2371, 2174 and 2012, respectively, disclosed by Kensil et al. (*Vaccine*, 92, 35–40, Cold Spring Harbor Laboratory Press). Therefore, it was confirmed that QS-L1 is a novel Quillaja saponin component.

EXAMPLE 3

Toxicity of the Saponin Components and Quil-A

With administration of crude Quillaja saponin components, a major symptom of toxicity in mice appears as necrosis of the liver. To investigate the toxicities of QS-L1, QS-L2, QS-L3, QS-L4, QS-L5 and Quil-A, 8-week old CD-1 male mice(Charle's River Institute, Japan) were injected intradermally with 125, 250 or 500 μg each of the saponin components and Quil-A as shown in Table III. The control group received physiological saline only.

TABLE III

| Injected | Number of Mice Injected | | | | | |
|---|---|---|---|---|---|---|
| Dose (μg) | Physiol. Saline | Quil-A | QS-L1 | QS-L2 | QS-L4 | QS-L5 |
| 125 | — | 5 | 5 | 5 | 5 | 5 |
| 250 | — | 5 | 5 | 5 | 5 | 5 |
| 500 | 5 | 5 | 5 | 5 | 5 | 5 |

As a result, the number of mice died within 72 hours from the administration of saponin components and Quil-A are shown in Table IV in comparison with the result disclosed by Kensil, C. R., et al.(*J. Immunol.*, 146, 431–437(1991)).

TABLE IV

Toxicity of Saponin Components on CD-1 Mice (a) Result of the present Example

| Injected | Number of Dead Mice/Injected Mice | | | | | |
|---|---|---|---|---|---|---|
| Dose (μg) | Physiol. Saline | Quil-A | QS-L1 | QS-L2 | QS-L4 | QS-L5 |
| 125 | — | 1/5 | 0/5 | 0/5 | 2/5 | 0/5 |
| 250 | — | 1/5 | 0/5 | 0/5 | 4/5 | 0/5 |
| 500 | 0/5 | 5/5 | 0/5 | 0/5 | 5/5 | 3/5 |

(b) Result disclosed by Kensil et al.

| Injected Dose | Number of Dead Mice/Injected Mice | | | |
|---|---|---|---|---|
| (μg) | Quil-A | QS-7 | QS-18 | QS-21 |
| 125 | 1/5 | 0/5 | 4/5 | 0/5 |
| 250 | 2/5 | 0/5 | 5/5 | 0/5 |
| 500 | 4/5 | 0/5 | 5/5 | 1/5 |

The result shows that Quil-A has a considerably high toxicity and the major cause thereof is QS-L4 which is presumed to be corresponding to QS-18. QS-L1 and QS-L2 exhibited little or no toxicity at a dosage level of 500 μg. QS-L5, which is presumed to be identical with QS-21, is believed to have a high toxicity because 3 mice were dead from the 5 mice injected with 500 μg dosage.

EXAMPLE 4

Hemolytic Activity of the Saponin Components

Hemolytic activity of QS-L1, QS-L2, QS-L3, QS-L4, QS-L5 and Quil-A was determined by using sheep red blood cell(SRBC) in accordance with the method of Kersten et al.(WO 92/06710) or Kensil et al.(U.S. Pat. No. 5,057,540 (1991)).

Figure 5:
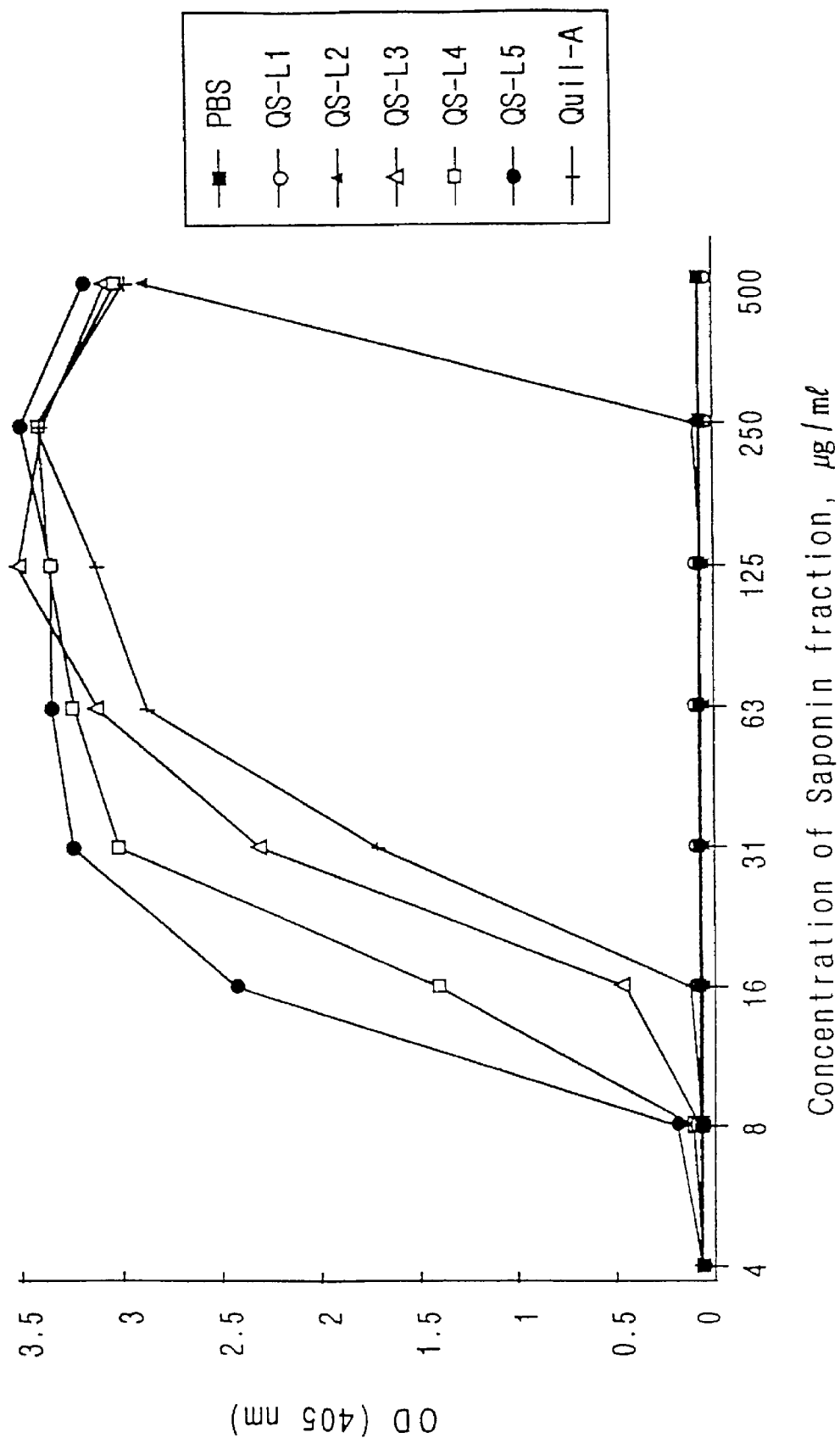
FIG. 5 presents hemolytic activities on sheep red blood cells of phosphate buffered saline(PBS), QS-L1, QS-L2, QS-L3, QS-L4, QS-L5 and Quil-A.

First, 500 μg/ml each of QS-L1, QS-L2, QS-L3, QS-L4, QS-L5 and Quil-A were diluted respectively by serial double dilution to a final concentration of 4 μg/ml. 5 ml of SRBC (Korea medical Co.), which is dispersed in Alserver's solution, was placed in 15 ml conical tube and then centrifuged at 2,000 rpm for 10 min. To the precipitated SRBC was added 10 ml of physiological saline and the mixture was centrifuged under the same condition as above. This washing process was repeated once more. The precipitated SRBC was recovered and dispersed in physiological saline to a final concentration of 4% (v/v). 150 µl each of the 4% SRBC solution was added to each well of a 96-well round-bottomed microtiter plate and the saponin component dilutions prepared above were added to the wells in an amount of 50 µl/well. After incubation at 37° C. for 30 min., the plate was centrifuged at 2,500 rpm for 10 min. by using a microplate centrifuge(Hanil, Korea) to sediment unhemolyzed cells. 100 µl of the supernatant from each well was transferred to the wells of flat-bottom microtiter plate and absorbance was determined at 405 nm with a Dynatech microtiter plate reader. The result is shown in FIG. 5, wherein QS-L3, QS-L4 and QS-L5 shows considerably high hemolytic activities at 20 µg/ml, while no hemolytic activity was observed with QS-L1 up to 500 µg/ml. This result shows that QS-L1 may be employed safely and effectively as an immune adjuvant for an antigen, which is optionally adsorbed on alum, at a concentration up to 500 µg/ml.

EXAMPLE 5

Immune Adjuvant Activity of the Saponin Components

Immune adjuvant Activity of saponin components QS-L1, QS-L2, QS-L3, QS-L4 and QS-L5 were determined in accordance with the same procedures as in the Reference Example, and the resulting antibody titers are shown in Table V.

TABLE V

Immune Adjuvant Activity of Saponin Components (Antibody Titer)

| | | Adjuvants | | | |
|---|---|---|---|---|---|
| Mouse No. | Alum | Alum + QS-L1 | Alum + QS-L2 | Alum + QS-L3 | Alum + QS-L4 | Alum + QS-L5 |
| 1 | 25600 | 102400 | 25600 | 51200 | 25600 | 51200 |
| 2 | 51200 | 204800 | 25600 | 204800 | 102400 | 25600 |
| 3 | 12800 | 102400 | 51200 | 51200 | 204800 | 204800 |
| 4 | 6400 | 51200 | 12800 | 51200 | 102400 | 102400 |
| 5 | 25600 | 204800 | 12800 | 51200 | 25600 | 102400 |
| Mean | 24320 | 133120 | 25600 | 81920 | 92160 | 97280 |
| S.D.* | 17173 | 68692 | 15677 | 68692 | 73753 | 68692 |

S.D.*: Standard deviation

Saponin components QS-L1, QS-L2, QS-L3, QS-L4 and QS-L5, when used in combination with alum, showed an immune adjuvant activity superior to alum which was used alone. Especially, alum+QS-L1 exhibited the highest immune adjuvant activity. Therefore, as can be seen from the results of Example 3 and the present Example, alum+QS-L1 will show excellent immune adjuvant activity than other pre-existing adjuvants, while showing little toxicity.

EXAMPLE 6

Vaccine Formulation Comprising Saponin Component QS-L1 as an Immune Adjuvant

The immune adjuvant activity of QS-L1 in a vaccine formulation, when used together with another immune adjuvant, was determined as follows.

First, 1 ml of EuVax(LG Chemical Ltd., Korea), which is a recombinant hepatitis B vaccine comprising 20 µg HBsAg/ 500 µg alum/ml, was mixed with 50 µl of QS-L1 solution, wherein saponin component QS-L1 is dissolved in distilled water to a concentration of 2 mg/ml, to prepare a hepatitis B vaccine formulation(Formulation 1) containing alum and QS-L1 as immune adjuvants. On the other hand, 1 ml of 20 µg/ml of free HBsAg, which is not adsorbed on alum, was mixed with 50 µl of 2 mg/ml QS-L1 to prepare a hepatitis B vaccine formulation(Formulation 2) containing QS-L1 only as an adjuvant. As a positive control, a hepatitis B vaccine formulation(Formulation 3) containing Freund's complete adjuvant(FCA) as an adjuvant, which is in the form of water-in-oil emulsion, was prepared by mixing FCA with the same amount of HBsAg to a concentration of 20 µg/ml.

50 µl each of Formulations 1, 2 and 3 and EuVax were injected subcutaneously to two spots in the back of a 7 to 8-week old female Balb/c mouse. 0.1 ml of Formulation 3, i.e., the FCA formulation, was injected peritoneally to the mouse.

Further immunization of the mice and determination of antibody titer were carried out in accordance with the same method as in the Reference Example, provided that FCA in Formulation 3 was replaced with Freund's incomplete adjuvant in the boost shots. The result is shown in Table VI.

TABLE IV

| | Adjuvants (Vaccine Formulations) | | | |
|---|---|---|---|---|
| Mouse No. | Alum (EuVax) | Alum + QS-L1 (Formulation 1) | QS-L1 (Formulation 2) | FCA (Formulation 3) |
| 1 | 51200 | 51200 | 12800 | 204800 |
| 2 | 51200 | 204800 | 6400 | 409600 |
| 3 | 51200 | 204800 | 6400 | 409600 |
| 4 | 102400 | 204800 | 51200 | 204800 |
| 5 | 25600 | 409600 | 25600 | 812000 |
| Mean | 56320 | 215040 | 20480 | 408160 |
| S.D.* | 28043 | 127487 | 18877 | 247892 |

S.D.*: Standard deviation

As can be seen from Table VI, QS-L1, when used alone, showed an immune adjuvant activity lower than alum used alone. However, when QS-L1 was used in combination with alum, it showed an enhanced immune adjuvant activity which is 3–4 times the activity of alum used alone. Accordingly, the alum+QS-L1 can be used as a immune adjuvant superior to alum alone. This result suggests a possible synergism between alum and saponin component QS-L1 to increase the immune adjuvant activity.

EXAMPLE 7

Effect of QS-L1 on Cellular Immune Response

The effect of QS-L1 on the cellular immune response was examined by determining the proliferation of spleen cells obtained from a mouse, which was injected with the hepatitis B vaccine formulations prepared in Example 6 and then treated with HBsAg. Proliferation of spleen cells were determined in accordance with the method of Byars et al.(*Vaccine*, 9, 309–317(1991)).

First, a mouse was immunized with the vaccine formulations prepared in Example 6, in accordance with the method of Reference Example. Two weeks after the last boosting, the spleen was aseptically removed from the mouse and spleen cells were obtained therefrom.

$2 \times 10^5$ spleen cells were placed in each well of a U-form 96-well incubation plate, said well containing RPMI-1640 medium comprising 10% fetal bovine serum and 2 mM glutamine. HBsAg was added to each well to a concentration of 1 µg/ml, except 4 wells which was used as a control group. The plate was incubated at 37° C. for 4 days under 7% $CO_2$ atmosphere.

When the culture was completed, 0.5 $\mu$Ci of $^3$H-thymidine (Amersham Cat. No. TRK 686) was added to each well and the plate was incubated for further 24 hours under the same conditions as above. The cells were collected by a cell harvester(Skatron) and the amount of $^3$H-thymidine incorporated in the cell was determined by using a liquid scintillation counter. The immune adjuvant activity of each adjuvant was represented by stimulation index(SI) which was calculated by the following equation:

$$SI = \frac{\text{cpm of a sample treated with HBsAg}}{\text{cpm of a sample not treated with HBsAg}}$$

The result was shown in FIGS. 6A and 6B, wherein two separate experiments were carried out by allotting two(FIG. 6A) or four(FIG. 6B) mice to each vaccine formulation. "Normal" means the spleen cells from a mouse not treated with HBsAg. The result shows that a vaccine containing QS-L1 in combination with alum shows much higher cellular immune response than the vaccine formulation containing alum alone.

While the invention has been described with respect to the above specific embodiments, it should be recognized that various modifications and changes may be made to the invention by those skilled in the art which also fall within the scope of the invention as defined by the appended claims.

What is claimed is:

1. A substantially pure saponin component separated from a Quillaja bark extract, having the designation of QS-L1, which is characterized by:
    a retention time of about 14 minutes when analyzed by reversed phase high pressure liquid chromatography (RP-HPLC) on a 4.6×250 mm Vydac C4 column using a 0.1 wt % trifluoroacetic acid solution in water/acetonitrile(7/3; v/v) at a flow rate of 1 ml/minute; and
    a molecular ion at m/z 979.4 when analyzed by ESI-MS.

2. A process for isolating the saponin component QS-L1 of claim 1 from the bark extract of *Quillaja saponaria Molina* which comprises:

(a) centrifuging a solution of the bark extract in an aqueous acetic acid solution to obtain a supernatant;

(b) dialyzing the supernatant against an aqueous acetic acid solution using an ultradialysis membrane having a molecular cut-off value ranging from 12 to 14 kDa;

(c) centrifuging the resulting dialyzate to obtain a second supernatant;

(d) lyophilizing the second supernatant to obtain a saponin extract powder; and (e) dissolving the saponin extract powder in a suitable solvent and subjecting the solution to RP-HPLC using a C4 RP-HPLC column under a linear concentration gradient of 30 to 40% acetonitrile containing 0.1% trifluoroacetic acid to obtain a fraction containing substantially pure QS-L1.

3. A vaccine formulation comprising an antigen, the saponin component QS-L1 of claim 1 as an immune adjuvant, and a second adjuvant.

4. The vaccine formulation of claim 3, wherein the second adjuvant is alum.

5. The vaccine formulation of claim 4, wherein the antigen is adsorbed on the alum.

6. The vaccine formulation of claim 3, wherein the antigen is hepatitis B viral surface antigen(HBsAg).

7. The vaccine formulation of claim 3, which comprises QS-L1 in an amount ranging from 1 to 500 $\mu$g/single dose.

8. A method for increasing the antigenicity of an antigen in a vaccine formulation which comprises employing the saponin component QS-L1 of claim 1 as an immune adjuvant in combination with a second adjuvant.

9. The method of claim 8, wherein the second adjuvant is alum.

10. The method of claim 8, wherein the amount of QS-L1 in the vaccine formulation ranges from 1 to 500 $\mu$g/single dose.

* * * * *

UNITED STATES PATENT AND TRADEMARK OFFICE

CERTIFICATE OF CORRECTION

PATENT NO.    : 5,817,314
DATED         : October 6, 1998
INVENTOR(S)   : Hong-Seob So, et al It is certified that error appears in the above-identified patent and that said Letters Patent is hereby corrected as shown below:

On the title page, item [30] should read
    Foreign Application Priority Data

Apr. 13, 1995   [KR]   Rep. of Korea      95-8590
  Apr. 13, 1995   [KR]   Rep. of Korea      95-8589

Signed and Sealed this

Fifth Day of January, 1999

Attest:

*Attesting Officer*        *Acting Commissioner of Patents and Trademarks*